United States Patent
Lei et al.

(10) Patent No.: US 11,198,665 B1
(45) Date of Patent: Dec. 14, 2021

(54) (Z)-SOLANONE, AND PREPARATION PROCESS AND USE THEREOF

(71) Applicant: CHINA TOBACCO YUNNAN INDUSTRIAL CO., LTD, Kunming (CN)

(72) Inventors: Sheng Lei, Kunming (CN); Zhihua Liu, Kunming (CN); Kai Wang, Kunming (CN); Zhenjie Li, Kunming (CN); Deshou Mao, Kunming (CN); Kunmiao Wang, Kunming (CN); Li Gao, Kunming (CN); Lei Fu, Kunming (CN); Yipeng Zhang, Kunming (CN); Wei Zhe, Kunming (CN); Ying Yang, Kunming (CN); Qianghui Zhou, Kunming (CN)

(73) Assignee: CHINA TOBACCO YUNNAN INDUSTRIAL CO., LTD, Kunming (CN)

( * ) Notice: Subject to any disclaimer, the term of this patent is extended or adjusted under 35 U.S.C. 154(b) by 0 days.

(21) Appl. No.: 17/287,999

(22) PCT Filed: Jun. 1, 2020

(86) PCT No.: PCT/CN2020/093673
§ 371 (c)(1),
(2) Date: Apr. 23, 2021

(87) PCT Pub. No.: WO2021/068530
PCT Pub. Date: Apr. 15, 2021

(30) Foreign Application Priority Data

Dec. 6, 2019 (CN) .................. 201911244805.X

(51) Int. Cl.
C07C 45/74 (2006.01)
A24B 15/32 (2006.01)
(52) U.S. Cl.
CPC .............. *C07C 45/74* (2013.01); *A24B 15/32* (2013.01)
(58) Field of Classification Search
CPC .................................................. C07C 45/74
See application file for complete search history.

(56) References Cited

U.S. PATENT DOCUMENTS

| 3,174,485 A | * | 3/1965 | Griffith .................. A24B 15/30 |
| | | | 131/276 |
| 4,433,695 A | * | 2/1984 | Hall ....................... A24B 15/32 |
| | | | 131/276 |
| 4,609,754 A | * | 9/1986 | Hall ....................... A24B 15/32 |
| | | | 512/25 |

FOREIGN PATENT DOCUMENTS

| CN | 105367517 A | * | 3/2016 | ............ C07C 45/00 |
| CN | 111004104 A | * | 4/2020 | |

* cited by examiner

Primary Examiner — Sikarl A Witherspoon
(74) Attorney, Agent, or Firm — Bayramoglu Law Offices LLC

(57) ABSTRACT

A (Z)-solanone has the steric formula of:

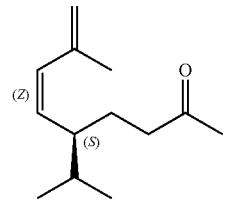

or

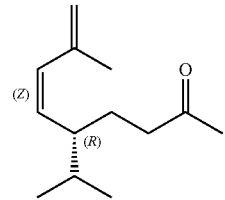

with the name of (S,Z)-5-isopropyl-8-methyl-6,8-diene-2-one or (R,Z)-5-isopropyl-8-methyl-6,8-diene-2-one. A process for the preparation of the (Z)-type solanone and the use thereof in flavoring of cigarette shred are further disclosed. The process includes the following steps: (1) reacting isopentanal and methyl vinyl ketone, under the action of a catalyst and a co-catalyst, to give (S)-2-isopropyl-5-carbonylhexanal or (R)-2-isopropyl-5-carbonylhexanal; (2) reacting the (S)-2-isopropyl-5-carbonylhexanal or the (R)-2-isopropyl-5-carbonylhexanal obtained in step (1) with (iodomethyl)triphenylphosphonium iodide, to give (S,Z)-7-iodo-5-isopropyl-6-ene-2-one or (R,Z)-7-iodo-5-isopropyl-6-ene-2-one; and (3) reacting the (S,Z)-7-iodo-5-isopropyl-6-ene-2-one or the (R,Z)-7-iodo-5-isopropyl-6-ene-2-one obtained in step (2) with pinacol isopropenylborate in the presence of a catalyst to give the (Z)-solanone.

5 Claims, No Drawings

(Z)-SOLANONE, AND PREPARATION PROCESS AND USE THEREOF

CROSS REFERENCE TO THE RELATED APPLICATIONS

This application is the national phase entry of International Application No. PCT/CN2020/093673, filed on Jun. 1, 2020, which is based upon and claims priority to Chinese Patent Application No. 201911244805.X, filed on Dec. 6, 2019, the entire contents of which are incorporated herein by reference.

TECHNICAL FIELD

The invention is in the technical field of organic synthesis, and particularly, it relates to a (Z)-solanone, a process for preparing same and use thereof in tobacco flavoring.

BACKGROUND

Cemb renoids are an important kind of terpenoids formed in the growth process of tobacco plants. This kind of materials per se do not have any fragrance, but they will be degraded in a series of processes of tobacco concocting, aging, and processing, to produce a number of compounds having flavors. Among primary degradation products of the materials, solanone is the most important flavor component. The solanone may be further degraded in the process of tobacco concocting and aging, to produce solanofuran, solanedione, solanesol, solanic acid and esters thereof, which have important impacts on tobacco tastes and flavors. The solanone is only contained in tobacco leaves in a very slight amount (only about 0.0036% based on the dry weight of the tobacco leaves), and thus, obtaining this kind of materials by an extraction method, obviously, does not have any application values. Hence, only by artificial synthesis methods, this demand can be satisfied.

When being used in the flavoring of tobacco products, the solanone enables tobacco flavors to be richer and fuller, mouthfeel to be improved, and the tobacco products to have fresh red tea flavor, faint flavor, grass flavor, carrot flavor or the like while having slightly sweet flavors. The solanone, when being added to any tobacco shred, will exhibit unique effects, and in the aspects of removing miscellaneous flavors, enhancing flavors and strength and coordinating with shred, by far, no spice is comparable to the solanone. The production of single spice for tobacco, as compared to the formulation of tobacco spices, will be more difficult, and especially the artificial synthesis of single spice, like solanone, will be very difficult. Domestic artificial synthesis routes of pure solanone single spice (with the consideration to steric configurations) are not developed in a breakthrough way at all time.

With regard to the domestic synthesis of solanone, more than ten synthesis methods are currently reported, and the preparations are primarily conducted with isopentanal, ethyl isovalerate, diethyl malonate or the like as raw materials. These synthesis methods mostly have long routes, and they use alkyl metal reagents that are sensitive to air and moisture, thereby to increase safe risks and costs in productions. In addition, in existing solanone synthesis methods, no one method considers controls to the steric configuration of products (R, S-configurations of C5 chiral carbon and E, Z-configurations of double bond between C6 and C7), and what are obtained in these methods are mixtures of various steric configurations of the solanone or racemates thereof, while the pure (Z)-solanone, like (S,Z)-5-isopropyl-8-methyl-6,8-diene-2-one or (R,Z)-5-isopropyl-8-methyl-6,8-diene-2-one, has not been obtained yet. In order to solve the above problem, the invention is proposed.

SUMMARY

The technical solution according to the invention is described as follows:

A first aspect of the invention discloses a (Z)-solanone, characterized in having the steric formula:

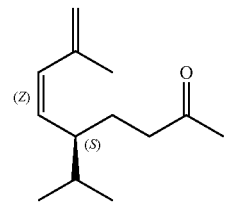

or

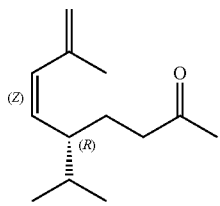

with the name of (S,Z)-5-isopropyl-8-methyl-6,8-diene-2-one or (R,Z)-5-isopropyl-8-methyl-6,8-diene-2-one.

A second aspect of the invention discloses a process for the preparation of the (S,Z)-solanone, comprising the following steps:

(1) reacting raw materials isopentanal and methyl vinyl ketone, under the action of a catalyst and a co-catalyst, to give a compound (S)-2-isopropyl-5-carbonylhexanal or (R)-2-isopropyl-5-carbonylhexanal;

(2) reacting the (S)-2-isopropyl-5-carbonylhexanal or the (R)-2-isopropyl-5-carbonylhexanal obtained in step (1) with (iodomethyl)triphenylphosphonium iodide, to give (S,Z)-7-iodo-5-isopropyl-6-ene-2-one or (R,Z)-7-iodo-5-isopropyl-6-ene-2-one;

(3) reacting the (S,Z)-7-iodo-5-isopropyl-6-ene-2-one or the (R,Z)-7-iodo-5-isopropyl-6-ene-2-one obtained in step (2) with pinacol isopropenylborate in the presence of a catalyst to give the (Z)-solanone: (S,Z)-5-isopropyl-8-methyl-6,8-diene-2-one or (R,Z)-5-isopropyl-8-methyl-6,8-diene-2-one;

wherein the reaction scheme is shown as follows:

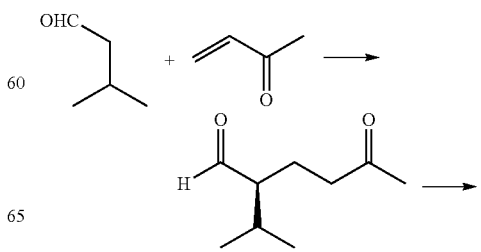

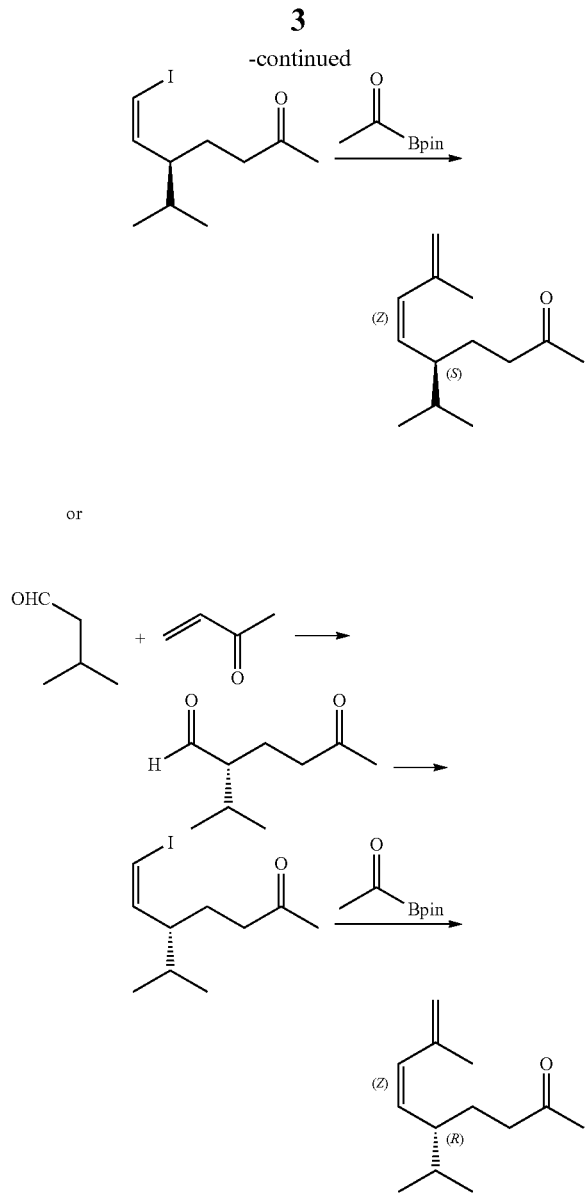

Preferably, the catalyst in step (1) is (S)-2-(methoxydiphenylmethyl)pyrrolidine or (R)-2-(methoxydiphenylmethyl)pyrrolidine, and the co-catalyst is ethyl 3,4-dihydroxybenzoate; the molar ratio of the raw materials, methyl vinyl ketone to isopentanal, is between 1:1.0 and 1:2.0; the molar ratio of 2-(methoxydiphenylmethyl)pyrrolidine to isopentanal is between 0.1:1.0 and 0.1:2.0; the molar ratio of ethyl 3,4-dihydroxybenzoate to isopentanal is between 0.2:1.0 and 0.2:2.0; the reaction temperature is from −10 to 50° C., and the reaction time is from 20 to 30 h.

Preferably, the reaction in step (2) is performed in a basic solvent, and an additive is added thereto; the solvent is tetrahydrofuran, the base is sodium hexamethyldisilylamide, and the additive is hexamethylphosphoric triamide; the molar ratio of 2-isopropyl-5-carbonylhexanal to (iodomethyl)triphenylphosphonium iodide is between 1:1.0 and 1:1.5; the molar ratio of 2-isopropyl-5-carbonylhexanal to sodium hexamethyldisilylamide is between 1:1.0 and 1:1.5; the molar ratio of 2-isopropyl-5-carbonylhexanal to hexamethylphosphoric triamide is between 1:4.0 and 1:5.0; the reaction temperature is from −100° C. to room temperature, and the reaction time is from 2 to 10 h; the room temperature is 40° C.; the hexamethylphosphoric triamide, being an excellent aprotic polar solvent, can increase the alkalinity and remarkably improve the reaction activity.

Preferably, the catalyst used in step (3) is [1,1′-bis(diphenylphosphino)ferrocene] palladium dichloride.

Preferably, the reaction in step (3) is performed in a basic solvent; the solvent is tetrahydrofuran; the base is sodium hydroxide; the molar ratio of 7-iodo-5-isopropyl-6-ene-2-one to pinacol isopropenylborate is between 1:1.0 and 1:2.0; the mole ratio of 7-iodo-5-isopropyl-6-ene-2-one to sodium hydroxide is between 1:1.5 and 1:2.5; the molar ratio of the catalyst to 7-iodo-5-isopropyl-6-ene-2-one is between 0.05:1.0 and 0.05:2.0; the reaction temperature is from 0 to 100° C., and the reaction time is from 2 to 10 h.

A third aspect of the invention discloses use of the (Z)-solanone for flavoring cigarette shred.

The invention has the following beneficial effects:

1. The pure (Z)-solanone according to the invention, (S,Z)-5-isopropyl-8-methyl-6,8-diene-2-one or (R,Z)-5-isopropyl-8-methyl-6,8-diene-2-one, is disclosed for the first time, and it is a novel compound.

2. The invention, starting from the cheap compounds isopentanal and methyl vinyl ketone, can prepare the pure target molecule (Z)-solanone only in three steps. The invention can precisely accomplish the artificial synthesis of pure (S,Z)-5-isopropyl-8-methyl-6,8-diene-2-ketone or (R,Z)-5-isopropyl-8-methyl-6,8-diene-2-ketone, with few synthesis steps and high safety. And the overall yield can reach more than 50%, which has the potential for industrialization.

3. The preparation process of the invention is added with a small amount of hexamethylphosphoric triamide. The hexamethylphosphoric triamide, being an excellent aprotic polar solvent, can increase the alkalinity and remarkably improve the reaction activity and yield.

4. The (Z)-solanone is used for flavoring cigarette shred, and it can remarkably increase richness and elegance of tobacco flavors, increase smoke concentration, improve smoke smoothness and fineness, improve smoking taste, cover miscellaneous flavors and return sweet aftertaste, thereby to exhibit a wide application prospect as a core spice of tobacco.

DETAILED DESCRIPTION OF THE EMBODIMENTS

The invention is further illustrated by the following examples that are intended only for better understanding the invention and but not for limiting the invention.

Example 1: Synthesis of (S)-2-isopropyl-5-carbonylhexanal or (R)-2-isopropyl-5-carbonylhexanal 73 mg (about 0.4 mmol) of ethyl 3,4-dihydroxybenzoate were placed in a round-bottom flask, and 53.48 mg (0.2 mmol) of (S)-2-(methoxydiphenylmethyl)pyrrolidine, 215 μL (about 2 mmol) of isopentanal and 243 μL (about 3 mmol) of methyl vinyl ketone were added thereto in order. The reaction mixture was stirred at room temperature to dissolve solids for 24 hours.

After the reaction was completed, the residual methyl vinyl ketone was removed by rotary evaporation, and the residual liquid was separated by a column chromatography with petroleum ether:ethyl acetate of 20:1, to produce 230.1 mg of a light yellow liquid, with the yield of 74%. The product was analyzed to be (S)-2-isopropyl-5-carbonylhexanal, i.e.,

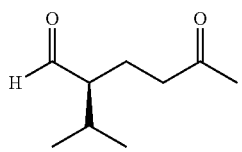

and the analyses were shown below:

$^1$H NMR (400 MHz, Chloroform-d) δ 9.59 ((d, J=2.8 Hz, 1H), 2.47 (m, 1H), 2.35 (m, 1H), 2.11 (s, 3H), 2.07-1.99 (m, 2H), 1.85-1.70 (m, 2H), 0.98 (d, J=6.6 Hz, 3H), 0.95 (d, J=6.6 Hz, 3H). $^{13}$C NMR (101 MHz, Chloroform-d) δ 208.05, 205.28, 57.50, 41.23, 29.97, 28.34, 20.25, 19.44, 19.31. [α] +47.754° (589 nm), (c 0.54 g/100 mL, CHCl$_3$).

Except for the use of (R)-2-(methoxydiphenylmethyl) pyrrolidine to replace the catalyst, the conditions were not changed. In this case, the yield was also 74%. The product was analysed to be (R)-2-isopropyl-5-carbonylhexanal, i.e.,

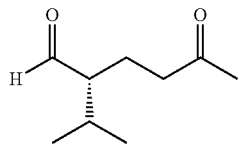

and the analyses were shown below:

$^1$H NMR (400 MHz, Chloroform-d) δ 9.59 (d, J=2.8 Hz, 1H), 2.47 (m, 1H), 2.35 (m, 1H), 2.11 (s, 3H), 2.07-1.97 (m, 2H), 1.86-1.69 (m, 2H), 0.98 (d, J=6.6 Hz, 3H), 0.95 (d, J=6.6 Hz, 3H). $^{13}$C NMR (101 MHz, Chloroform-d) δ 208.04, 205.28, 57.49, 41.23, 29.97, 28.33, 20.24, 19.44, 19.32. [α] –47.128° (589 nm), (c 0.54 g/100 mL, CHCl$_3$).

Example 2: Synthesis of (S,Z)-7-iodo-5-isopropyl-6-ene-2-one or (R,Z)-7-iodo-5-isopropyl-6-ene-2-one 1166 mg (about 2.2 mmol) of (iodomethyl)triphenylphosphonium iodide were placed in a reaction flask, and 3 mL of tetrahydrofuran and 1.1 mL of a 2M (about 2.2 mmol) tetrahydrofuran solution of sodium hexamethyldisilylamide were added thereto. The system, after being stirred at room temperature for 15 minutes, became bright red. The system was cooled to –78° C. and added with 1.6 mL (about 9.2 mmol) of hexamethylphosphoric triamide, and finally, 312 mg (about 2 mmol) of a mixed solution of the (S)-2-isopropyl-5-carbonylhexanal obtained in Example 1 in 2 mL of tetrahydrofuran were added thereto. The mixture was stirred at –78° C. for 4 hours.

After the reaction was completed, the system was added with 2 mL of a saturated sodium bicarbonate solution and then filtered with diatomite, and the filtrate was extracted with ethyl acetate three times. The organic phases were combined and dried with anhydrous sodium sulfate and then concentrated, and the residual liquid was subjected to a column chromatography with petroleum ether:ethyl acetate of 30:1, to give 387 mg of a pale yellow liquid, with the yield of 69%. The product was analyzed to be (S,Z)-7-iodo-5-isopropyl-6-ene-2-one, i.e.,

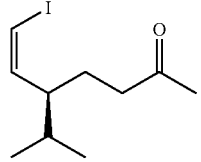

and the analyses was below:

$^1$H NMR (400 MHz, Chloroform-d) δ 6.31 (d, J=7.4 Hz, 1H), 5.86 (dd, J=9.8, 7.4 Hz, 1H), 2.49-2.31 (m, 2H), 2.24 (m, 1H), 2.12 (s, 3H), 1.82 (m, 1H), 1.69 (m, 1H), 1.50 (m, 1H), 0.92 (d, J=6.8 Hz, 3H), 0.88 (d, J=6.9 Hz, 3H). $^{13}$C NMR (101 MHz, Chloroform-d) δ 208.83, 143.31, 83.88, 50.03, 41.21, 31.86, 30.13, 25.29, 20.35, 19.23. [α]+ 34.839° (589 nm), (c 0.62 g/100 mL, CHCl$_3$).

Except for the use of (R)-2-isopropyl-5-carbonylhexanal obtained in Example 1, the conditions were not changed. In this case, 380 mg of a pale yellow liquid were obtained, with the yield of 68%. The product was analysed to be (R,Z)-7-iodo-5-isopropyl-6-ene-2-one, i.e.,

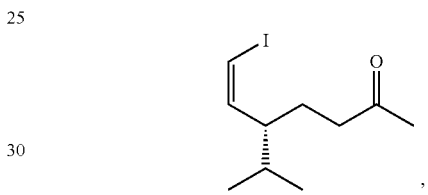

and the analyses were below:

$^1$H NMR (400 MHz, Chloroform-d) δ 6.31 (d, J=7.4 Hz, 1H), 5.86 (dd, J=9.8, 7.4 Hz, 1H), 2.44-2.35 (m, 2H), 2.24 (m, 1H), 2.12 (s, 3H), 1.82 (m, 1H), 1.69 (m, 1H), 1.50 (m, 1H), 0.92 (d, J=6.8 Hz, 3H), 0.88 (d, J=6.9 Hz, 3H). $^{13}$C NMR (101 MHz, Chloroform-d) δ 208.83, 143.31, 83.88, 50.03, 41.21, 31.86, 30.13, 25.29, 20.35, 19.23. [α] –34.032° (589 nm), (c 0.62 g/100 mL, CHCl$_3$).

Example 3: Synthesis of (5S,6Z)-solanone or (5R,6Z)-solanone 731 mg (about 1 mmol) of [1,1'-bis(diphenylphosphino)ferrocene]palladium dichloride were placed in a reaction tube, and 70 mL of tetrahydrofuran were added thereto. 2802 mg (about 10 mmol) of (S,Z)-7-iodo-5-isopropyl-6-ene-2-one obtained in Example 2 and 2.8 mL (about 15 mmol) of pinacol isopropenylborate were mixed in tetrahydrofuran to obtain 30 mL of a mixed solution, and 30 mL of the mixed solution were added to the above reaction tube. Finally, 10 mL (about 20 mmol) of a 2M sodium hydroxide aqueous solution were added to the above reaction tube and stirred at 60° C. for 5 hours.

After the reaction was completed, the system was added with water and then extracted with diethyl ether three times. The organic phases were combined and dried with anhydrous sodium sulfate and then concentrated to produce a crude product. The crude product was separated by a column chromatography with petroleum ether:ethyl acetate of 30:1, to give 1425 mg of a pale yellow liquid, with the yield of 73%. The product was analyzed to be (5S,6Z)-solanone i.e., (S,Z)-5-isopropyl-8-methyl-6,8-diene-2-ketone, i.e.,

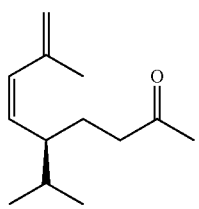

The analyses were shown below:

$^1$H NMR (400 MHz, Chloroform-d) δ 5.97 (d, J=12.0 Hz, 1H), 5.09 (t, J=11.6 Hz, 1H), 4.95-4.81 (m, 3H), 2.45-2.43 (m, 1H), 2.41-2.30 (m, 2H), 2.10 (s, 3H), 1.85 (s, 3H), 1.81-1.77 (m, 1H), 1.6-1.51 (m, 1H), 1.37 (m, 1H), 0.92-0.89 (d, J=6.8 Hz, 3H), 0.89-0.86 (d, J=6.8 Hz, 3H). $^{13}$C NMR (101 MHz, Chloroform-d) δ 209.34, 141.83, 133.67, 132.36, 115.43, 42.90, 41.94, 32.48, 29.98, 26.41, 23.53, 20.23, 19.52. [α] +9.355° (589 nm), (c 0.62 g/100 mL, CHCl$_3$).

Except for the use of (R,Z)-7-iodo-5-isopropyl-6-ene-2-one obtained in Example 2, the conditions were not changed. 1345 mg of a pale yellow liquid were obtained, with the yield of 69%. The product was analysed to be (5R,6Z)-solanone i.e., (R,Z)-5-isopropyl-8-methyl-6,8-diene-2-ketone, i.e.,

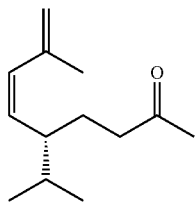

The analyses were shown below:

$^1$H NMR (400 MHz, Chloroform-d) δ 5.97 (d, J=12.0 Hz, 1H), 5.09 (t, J=11.6 Hz, 1H), 4.87 (m, 3H), 2.50-2.43 (m, 1H), 2.42-2.32 (m, 2H), 2.11 (s, 3H), 1.85 (s, 3H), 1.82-1.75 (m, 1H), 1.56 (m, 1H), 1.37 (m, 1H), 0.90 (d, J=6.8 Hz, 3H), 0.87 (d, J=6.9 Hz, 3H). $^{13}$C NMR (101 MHz, Chloroform-d) δ 209.34, 141.83, 133.67, 132.36, 115.42, 42.90, 41.94, 32.47, 29.97, 26.40, 23.53, 20.23, 19.52. [α] −9.839° (589 nm), (c 0.62 g/100 mL, CHCl$_3$).

Example 4: Applications of (Z)-solanone in Flavouring of Cigarette Shred

By taking sample cigarette with a brand produced in Yunnan Province as the experimental object, the quantity of added spices was calculated according to the weight of cigarette shred. The two pure (Z)-solanones synthesized according to the invention, (S,Z)-5-isopropyl-8-methyl-6,8-diene-2-ketone (an injection flavoured cigarette, cited as Sample 1) and (R,Z)-5-isopropyl-8-methyl-6,8-diene-2-ketone (an injection flavoured cigarette, cited as Sample 2), were formulated into an ethanol solution having a certain concentration. With a CIJECTOR essence and spice injector, according to the weight percent 0.005% of the spice in the shred, the ethanol solution was uniformly injected into cigarette; at equivalent conditions, ethanol in the same volume was injected to cigarette (cited as Sample 0) as a control. All samples was balanced at 22° C. and in a relative humidity of 60% for 48 hours. According to the tobacco industrial standards "Tobacco Product—Sensory Evaluation Methods" (YC/T415-2011), the three samples were subjected to sensory comparison evaluations, and the evaluation results were shown in the table below:

| | | Sample No. | | |
| --- | --- | --- | --- | --- |
| | | 0 | 1 | 2 |
| Fragrance characteristics | Fragrance quality | 7 | 7.5 | 7.5 |
| | Fragrance quantity | 6.5 | 7 | 7 |
| | Permeability | 6.5 | 7 | 7 |
| | Miscellaneous flavour | 7 | 7.5 | 7.5 |
| Smoke characteristics | Concentration | 6 | 6.5 | 6 |
| | Strength | 6 | 6 | 6 |
| | Fineness | 6.5 | 7 | 7 |
| | Cloud formation | 6 | 6.5 | 6.5 |
| Mouthfeel characteristics | Stimulation | 7.5 | 7 | 7.5 |
| | Dryness | 7 | 6.5 | 7 |
| | Cleanness | 7 | 7 | 7 |
| | Sweet | 7 | 7 | 7.5 |
| Total score | | 80 | 82.5 | 83.5 |

Note: a 9-score evaluation method

As seen from the sensory evaluation results, as compared to the control sample, due to the addition of (Z)-solanone, the two examples are conferred with remarkable characteristic fragrances of mature tobacco fragrance, dry grass fragrance, fresh and sweet fragrance or the like, which are in good harmony with initial fragrance of tobacco, increased in richness, fineness, and elegancy of tobacco fragrance and smoke plumpness, and remarkably improved in smoothness and fineness of smoke, and they can further cover miscellaneous flavours and improve aftertaste. By comparing the flavouring effects of the two isomer spices, the (S,Z)-solanone primarily has remarkable enhancing effects in quality and plumpness of fragrance and smoke state; the (R,Z)-solanone primarily has remarkable enhancing effects in richness of tobacco fragrance, fineness and elegancy of smoke, and sweetness and comfortability of aftertaste. In general, the two (Z)-solanones have the enhancing effects in the aspects of richness, plumpness and quality of cigarette fragrance, fineness and elegancy of smoke, and miscellaneous flavour reduction. The two isomers generally have similar effects which are slightly different in the emphases, and thus they have very high values in flavouring formulas of cigarette essences and spices.

What is claimed is:

1. A process for a preparation of (Z)-solanone, comprising the following steps:
    (1) performing a first reaction on isopentanal and methyl vinyl ketone, under an action of a first catalyst and a co-catalyst, to give (S)-2-isopropyl-5-carbonylhexanal or (R)-2-isopropyl-5-carbonylhexanal;
    (2) performing a second reaction on the (S)-2-isopropyl-5-carbonylhexanal or the (R)-2-isopropyl-5-carbonylhexanal obtained in step (1) and (iodomethyl)triphenylphosphonium iodide, to give (S,Z)-7-iodo-5-isopropyl-6-ene-2-one or (R,Z)-7-iodo-5-isopropyl-6-ene-2-one;
    (3) performing a third reaction on the (S,Z)-7-iodo-5-isopropyl-6-ene-2-one or the (R,Z)-7-iodo-5-isopropyl-6-ene-2-one obtained in step (2) and pinacol isopropenylborate in a presence of a second catalyst to give the (Z)-solanone, wherein a name of the (Z)-solanone is (S,Z)-5-isopropyl-8-methyl-6,8-diene-2-one or (R,Z)-5-isopropyl-8-methyl-6, 8-diene-2-one;

wherein a reaction scheme of the process is shown as follows:

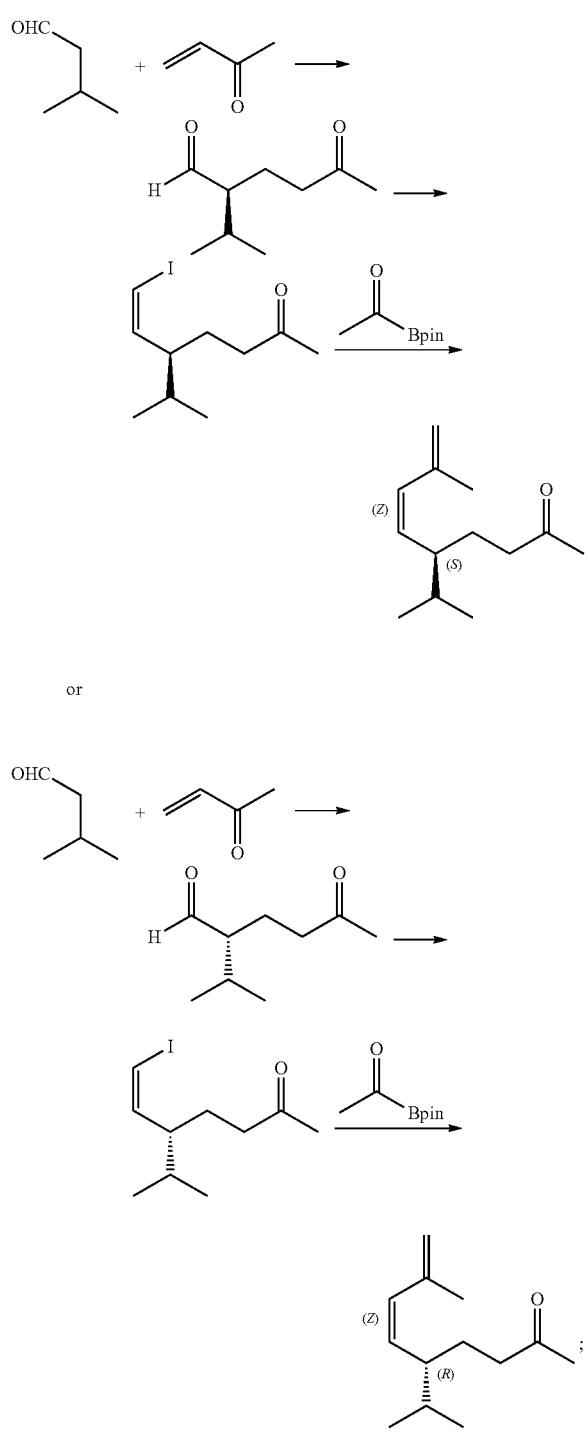

or wherein a steric formula of the (Z)-solanone is:

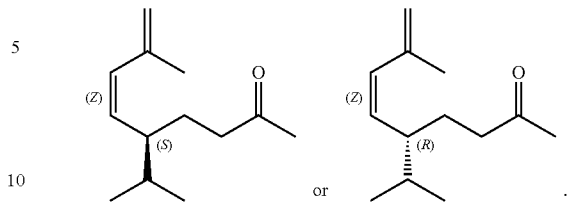

2. The process according to claim 1, wherein the first catalyst in step (1) is (S)-2-(methoxydiphenylmethyl)pyrrolidine or (R)-2-(methoxydiphenylmethyl)pyrrolidine, and the co-catalyst is ethyl 3,4-dihydroxybenzoate; a molar ratio of the methyl vinyl ketone to the isopentanal is between 1:1.0 and 1:2.0; a molar ratio of the (S)-2-(methoxydiphenylmethyl)pyrrolidine or the (R)-2-(methoxydiphenylmethyl)pyrrolidine to the isopentanal is between 0.1:1.0 and 0.1:2.0; a molar ratio of the ethyl 3,4-dihydroxybenzoate to the isopentanal is between 0.2:1.0 and 0.2:2.0; a reaction temperature of the first reaction is from −10 to 50° C., and a reaction time of the first reaction is from 20 to 30 h.

3. The process according to claim 1, wherein the second reaction in step (2) is performed under a condition of a basic solvent and adding an additive; a solvent of the basic solvent is tetrahydrofuran, a base of the basic solvent is sodium hexamethyldisilylamide, and the additive is hexamethylphosphoric triamide; a molar ratio of the (S)-2-isopropyl-5-carbonylhexanal or the (R)-2-isopropyl-5-carbonylhexanal to the (iodomethyl)triphenylphosphonium iodide is between 1:1.0 and 1:1.5; a molar ratio of the (S)-2-isopropyl-5-carbonylhexanal or the (R)-2-isopropyl-5-carbonylhexanal to the sodium hexamethyldisilylamide is between 1:1.0 and 1:1.5; a molar ratio of the (S)-2-isopropyl-5-carbonylhexanal or the (R)-2-isopropyl-5-carbonylhexanal to the hexamethylphosphoric triamide is between 1:4.0 and 1:5.0; a reaction temperature of the second reaction is from −100° C. to room temperature, and a reaction time of the second reaction is from 2 to 10 h; the room temperature is 40° C.

4. The process according to claim 1, wherein the second catalyst used in step (3) is [1,1′-bis(diphenylphosphino)ferrocene] palladium dichloride.

5. The process according to claim 1, wherein the third reaction in step (3) is performed in a basic solvent; a solvent of the basic solvent is tetrahydrofuran; a base of the basic solvent is sodium hydroxide; a molar ratio of the (S,Z)-7-iodo-5-isopropyl-6-ene-2-one or the (R,Z)-7-iodo-5-isopropyl-6-ene-2-one to the pinacol isopropenylborate is between 1:1.0 and 1:2.0; a mole ratio of the (S,Z)-7-iodo-5-isopropyl-6-ene-2-one or the (R,Z)-7-iodo-5-isopropyl-6-ene-2-one to the sodium hydroxide is between 1:1.5 and 1:2.5; a molar ratio of the second catalyst to the (S,Z)-7-iodo-5-isopropyl-6-ene-2-one or the (R,Z)-7-iodo-5-isopropyl-6-ene-2-one is between 0.05:1.0 and 0.05:2.0; a reaction temperature of the third reaction is from 0 to 100° C., and a reaction time of the third reaction is from 2 to 10 h.

* * * * *

UNITED STATES PATENT AND TRADEMARK OFFICE
CERTIFICATE OF CORRECTION

PATENT NO. : 11,198,665 B1
APPLICATION NO. : 17/287999
DATED : December 14, 2021
INVENTOR(S) : Sheng Lei et al.

Page 1 of 1

It is certified that error appears in the above-identified patent and that said Letters Patent is hereby corrected as shown below:

In the Specification

In Column 3 and 9, the four figures, should read:

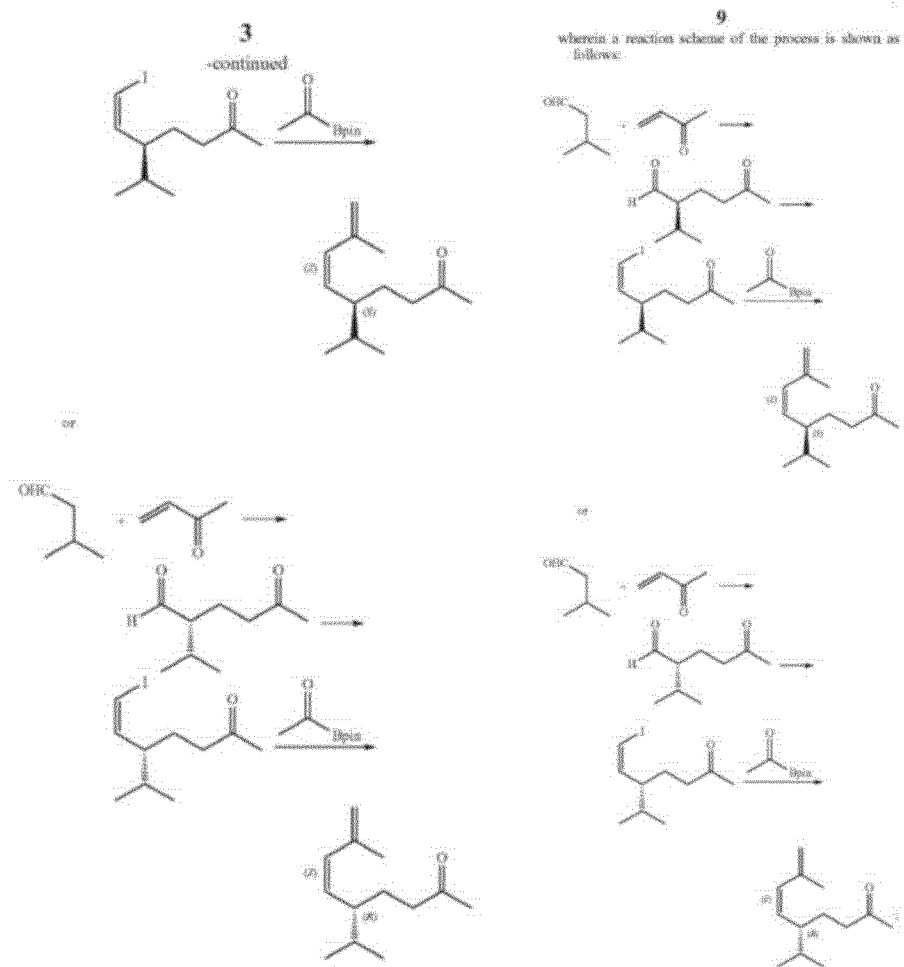

Signed and Sealed this
Thirteenth Day of December, 2022

Katherine Kelly Vidal
*Director of the United States Patent and Trademark Office*